United States Patent
Peng et al.

(10) Patent No.: US 8,022,238 B2
(45) Date of Patent: Sep. 20, 2011

(54) PHOSPHATE SURFACTANTS

(75) Inventors: Sheng Peng, Hockessin, DE (US); Allison Mary Yake, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 298 days.

(21) Appl. No.: 12/408,074

(22) Filed: Mar. 20, 2009

(65) Prior Publication Data

US 2010/0240920 A1    Sep. 23, 2010

(51) Int. Cl.
*C07F 9/02* (2006.01)
(52) U.S. Cl. ........................................ 558/169; 558/175
(58) Field of Classification Search .................. 558/169, 558/175
See application file for complete search history.

(56) References Cited

U.S. PATENT DOCUMENTS

| | | | |
|---|---|---|---|
| 5,585,516 A | 12/1996 | Varadaraj et al. | |
| 5,643,864 A | 7/1997 | Li et al. | |
| 5,656,586 A | 8/1997 | Li et al. | |
| 6,121,222 A | 9/2000 | Li et al. | |
| 6,399,202 B1 | 6/2002 | Yu et al. | |
| 7,470,818 B2 * | 12/2008 | Peng et al. | 568/8 |
| 2005/0132931 A1 | 6/2005 | Ham et al. | |
| 2007/0099018 A1 | 5/2007 | Shtarov et al. | |
| 2007/0295957 A1 | 12/2007 | Lee et al. | |
| 2008/0028986 A1 | 2/2008 | Futterer et al. | |
| 2008/0033106 A1 | 2/2008 | Koroskenyi et al. | |
| 2008/0093582 A1 | 4/2008 | Nagai et al. | |
| 2008/0113200 A1 | 5/2008 | Peng et al. | |
| 2009/0038510 A1 | 2/2009 | Acosta et al. | |
| 2009/0101508 A1 | 4/2009 | Combellas et al. | |

FOREIGN PATENT DOCUMENTS

| | | |
|---|---|---|
| EP | 1882528 | 1/2008 |
| WO | 2000027890 | 5/2000 |
| WO | 2008027604 | 3/2008 |
| WO | 2009/020906 A2 | 2/2009 |

* cited by examiner

*Primary Examiner* — Rei-tsang Shiao
(74) *Attorney, Agent, or Firm* — Nancy S. Mayer

(57) ABSTRACT

A compound of Formula 1

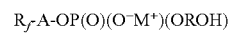

$R_f\text{-A-OP(O)(O}^-M^+\text{)(OROH)}$    Formula 1 wherein
 $R_f$ is a $C_2$ to $C_6$ linear or branched perfluoroalkyl optionally interrupted by one, two or three ether oxygen atoms;
 A is $(CH_2CF_2)_m(CH_2)_n-$, $(CH_2)_oSO_2N(CH_3)(CH_2)_p-$, $O(CF_2)_q(CH_2)_r-$, or $OCHFCF_2OE-$;
 m is 0 to 4; n, o, p, and r are each independently 2 to 20; q is 2;
 E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
 M is H or a Group I metal or an ammonium cation $(NH_xR^2_y)^+$ wherein $R^2$ is a $C_1$ to $C_4$ alkyl, x is 0 to 4, y is 0 to 4 and x+y is 4; and
 R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2.

21 Claims, No Drawings

PHOSPHATE SURFACTANTS

FIELD OF INVENTION

The field of invention is fluorochemical surfactants, in particular phosphate surfactants which contain a hydrocarbon diol or polyalkylene glycol hydrophilic tail and a fluorinated hydrophobic tail.

BACKGROUND OF INVENTION

For surfactants and surface treatment agents with fluorochemical chains, longer perfluoroalkyl chains contain a higher percentage of fluorine at a given concentration and typically provide better performance. However, the fluorinated materials derived from longer perfluoroalkyl chains are more expensive. Reduction of the fluorine content with delivery of the same or higher performance is therefore desirable. Reducing the fluorine content would reduce the cost, but it is necessary to maintain product performance.

U.S. Ser. No. 11/890,414 filed Aug. 8, 2007, discloses fluoroalkyl-alkyl twin tailed phosphate surfactants which have two dissimilar terminal hydrophobic groups attached to a single connecting group. U.S. Pat. No. 5,643,864 discloses anionic surfactants having at least two hydrophobic chains and at least two hydrophilic groups per molecule useful as emulsifiers, detergents, dispersant and solubilizing agents.

It is desirable to improve surfactant performance, in particular lowering of surface tension in aqueous systems, and to increase the fluorine efficiency, i.e., boost the efficiency or performance of the surfactants so a lower proportion of the expensive fluorine component is required to achieve the same level of performance, or to have better performance using the same level of fluorine. Especially desirable would be surfactants having both a hydrophobic and a hydrophilic group in the same compound which are fluorine efficient. It is also desirable to have surfactants that are stable in brine and aggressive media (acid and base) while still maintaining improved performance. The present invention provides such surfactants.

SUMMARY OF THE INVENTION

The present invention comprises a compound of Formula 1

wherein $R_f$ is a $C_2$ to $C_6$ linear or branched perfluoroalkyl optionally interrupted by one, two or three ether oxygen atoms;

A is $(CH_2CF_2)_m(CH_2)_n$—, $(CH_2)_oSO_2N(CH_3)(CH_2)_p$—, $O(CF_2)_q(CH_2)_r$—, or $OCHFCF_2OE$-;

m is 0 to 4; n, o, p, and r are each independently 2 to 20; q is 2;

E is a $C_2$ to $C_{20}$ linear or branched alkyl group optionally interrupted by oxygen, sulfur, or nitrogen atoms; a cyclic alkyl group, or a $C_6$ to $C_{10}$ aryl group;

M is H or a Group I metal or an ammonium cation $(NH_xR^2_y)^+$ wherein $R^2$ is a $C_1$ to $C_4$ alkyl, x is 0 to 4, y is 0 to 4 and x+y is 4; and R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2.

The present invention further comprises a method of lowering the surface tension of an aqueous medium comprising contacting the medium with a composition of Formula 1 as defined above.

The present invention further comprises a method of providing soil repellency, leveling, and resistance to blocking to a coated substrate comprising adding to a coating base prior to deposition on the substrate a compound of Formula 1 as defined above.

DETAILED DESCRIPTION

Trademarks are shown herein in upper case.

The term "aggressive medium" as used herein means an acidic solution having a maximum pH of about 4, or a basic solution having a pH of at least about 10.

The present invention comprises a compound of Formula 1

wherein $R_f$ is a $C_2$ to $C_6$ linear or branched perfluoroalkyl optionally interrupted by one, two or three ether oxygen atoms;

A is $(CH_2CF_2)_m(CH_2)_n$—, $(CH_2)_oSO_2N(CH_3)(CH_2)_p$—, $O(CF_2)_q(CH_2)_r$—, or $OCHFCF_2OE$-;

m is 0 to 4; n, o, p, and r are each independently 2 to 20; q is 2;

E is a $C_2$ to $C_{20}$ linear or branched alkyl group optionally interrupted by oxygen, sulfur, or nitrogen atoms; a cyclic alkyl group, or a $C_6$ to $C_{10}$ aryl group;

M is H or a Group I metal or an ammonium cation $(NH_xR^2_y)^+$ wherein $R^2$ is a $C_1$ to $C_4$ alkyl, x is 0 to 4, y is 0 to 4 and x+y is 4; and R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2.

Preferred are compounds of Formula 1 wherein $R_f$ is a $C_3$ to $C_6$ perfluoroalkyl. Also preferred are those wherein $R_f$ is $C_3$, $C_4$ or $C_6$ perfluoroalkyl. Also preferred are compounds of Formula 1 wherein M is sodium or potassium or an ammonium cation $(NH_xR^2_y)^+$ wherein $R^2$ is a $C_1$ to $C_4$ alkyl, x is 0 to 4, y is 0 to 4 and x+y is 4. More preferred are compounds of Formula 1 wherein M is an ammonium cation $(NH_xR^2_y)^+$ wherein $R^2$ is a $C_1$ to $C_4$ alkyl, x is 0 to 4, y is 0 to 4 and x+y is 4. Also preferred are compounds of Formula 1 wherein E is a $C_2$ to $C_{20}$ linear or branched alkyl group optionally interrupted by oxygen. More preferred are compounds of Formula 1 wherein E is a $C_2$ to $C_{10}$ linear or branched alkyl group optionally interrupted by oxygen.

Other preferred compounds of Formula 1 are those wherein R is a linear or branched $C_2$ to $C_8$ alkyl, and more preferably $C_3$ alkyl. Other preferred compounds of Formula 1 are those wherein R is a $C_8$ to $C_{60}$, more preferably $C_8$ to $C_{40}$, linear or branched alkyl group optionally interrupted by oxygen atoms. When R is greater than 8 carbon atoms, the ratio of hetero atoms to carbon atoms is at least 1:2, preferably from about 1:2 to about 1:3.

In one embodiment R is a linear or branched alkyl group of about 8 to about 50 carbon atoms, and more preferably about 8 to 40 carbon atoms, interrupted by about 2 to about 20 ether oxygen atoms, wherein the ratio of ether oxygen atoms to carbon atoms is from about 1:2 to about 1:4; more preferably from about 1:2 to about 1:3. Within these compounds, preferably the R group has a molecular weight of between about 200 to about 1250.

Formula 1 is a surfactant containing both a hydrophobic group and a hydrophilic group. The compounds of Formula 1 are prepared by reacting either phosphorus pentoxide ($P_2O_5$) or phosphorus oxychloride ($POCl_3$) with fluorinated alcohol, followed by the addition of hydrocarbon diol or poly(glycol). Typically the phosphorus pentoxide or phosphorus oxychloride is added to the fluorinated alcohol in an amount that is approximately equivalent mol percent. For example, when phosphorus pentoxide is used from about 0.4 to about 1.6 mole equivalent of fluorinated alcohol to $P_2O_5$ is added. The mixture is heated to a temperature of from about 70° C. to about 120° C., preferably to from about 100° C. to about 110° C., and maintained for several hours, preferably from about 3 to about 15 hours. A diol or poly(glycol) is then added to the reaction mixture with continued heating at the above temperature for an additional time of from about 3 to about 15 hours. The mole ratio of diol or poly(glycol) to $P_2O_5$ is from about 1.4 to about 2.6. This is followed by the optional addition of a surfactant in from about 1% to about 3% by weight. Any of a variety of surfactants can be employed, such as TERGITOL available from Sigma Aldrich, St. Louis, Mo. After about 1 to about 2 hours, ammonia is added with mixing, followed by water, to provide the phosphate of Formula 1.

Diols useful in the synthesis of compounds of Formula 1 include $C_2$ to $C_{60}$ straight and branched chain alcohols optionally having one or two double bonds. Examples include 1,3-propanediol; propylene glycol(1,2-propanediol); di(ethylene glycol); tri(ethylene glycol); tetra(ethylene glycol); poly(ethylene glycol)s [PEG(OH)$_2$], preferably having from about 4 to about 20 repeat units, and more preferably from about 5 to about 15 repeat units; poly(ethylene glycol)-polypropylene glycol-poly(ethylene glycol) triblock polymers [PEG-PPG-PEG-(OH)$_2$]; and random copolymers of ethylene oxide and propylene oxide, preferably with a molecular weight $M_w$ of from about 200 to about 1250. Poly(1.3-propanediol)s are available from E. I. du Pont de Nemours and Company, Wilmington, Del. Polyethylene glycols with nominal molecular weights of 200 to 2000 are available from Aldrich Chemical Company, St. Louis, Mo. Tri-block copolymers of polyethylene oxide and polypropylene oxide (PEG-PPG-PEG) are available from BASF, Mount Olive, N.J.

The fluoroalkyl alcohol used as a reactant in the preparation of Formula 1 compounds are described below for various embodiments.

One embodiment of the invention is a compound of Formula 1 wherein A is $(CH_2CF_2)_m(CH_2)_n$—, herein denoted as Formula 2, $$R_f—(CH_2CF_2)_m(CH_2)_n—O—P(O)(O^-M^+)'(OROH) \quad \text{Formula 2}$$

wherein $R_f$, R, m, n, and M are as defined above in Formula 1. Preferred compounds of Formula 2 include those wherein $R_f$ is a $C_4$ or $C_6$ perfluoroalkyl, n is 2, R is $CH_2CH_2$, and m is 0, 1, or 2.

Fluorinated alcohols useful in the preparation of various embodiments of Formula 2 are available commercially or by synthesis. Fluorinated alcohols $C_6F_{13}CH_2CH_2OH$ and $C_4F_9CH_2CH_2OH$ are available from E. I. du Pont de Nemours and Company, Wilmington, Del. Fluorinated alcohols are available by synthesis according to the following Scheme 1:

Scheme 1

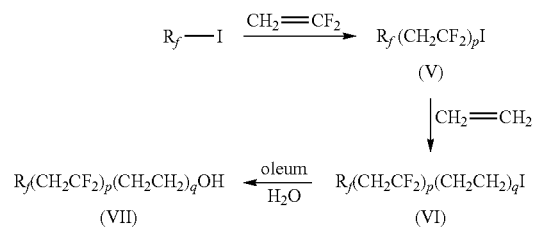

The telomerization of vinylidene fluoride (VDF) with linear or branched perfluoroalkyl iodides is well known, and produces compounds of the structure $R_f(CH_2CF_2)_pI$, wherein, p is 1 to 3 or more and $R_f$ is a $C_1$ to $C_6$ perfluoroalkyl group. For example, see Balague, et al, "Synthesis of fluorinated telomers, Part 1, Telomerization of vinylidene fluoride with perfluoroalkyl iodides", J. Flour Chem. (1995), 70(2), 215-23. The specific telomer iodides (V) in Scheme 1 are isolated by fractional distillation. The telomer iodides (V) can be treated with ethylene by procedures described in U.S. Pat. No. 3,979,469, (Ciba-Geigy, 1976) to provide the telomer ethylene iodides (VI) wherein q is 1 to 3 or more. The telomer ethylene iodides (VI) of Scheme 1 can be treated with oleum and hydrolyzed to provide the corresponding telomer alcohols (VII) according to procedures disclosed in WO 95/11877 (Elf Atochem S.A.). The higher homologs (q=2, 3) of telomer ethylene iodides (VI) are available with excess ethylene at high pressure. The telomer ethylene iodides (VI) can be treated with a variety of reagents to provide the corresponding thiols according to procedures described in J. Fluorine Chemistry, 104, 2 173-183 (2000). One example is the reaction of the telomer ethylene iodides (VI) with sodium thioacetate, followed by hydrolysis.

A further embodiment of the invention is a compound of Formula 1 wherein A is $(CH_2)_oSO_2N(CH_3)(CH_2)_p$—, herein denoted as Formula 3,

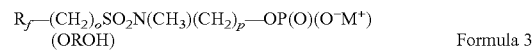

$$R_f—(CH_2)_oSO_2N(CH_3)(CH_2)_p—OP(O)(O^-M^+) \\ (OROH) \quad \text{Formula 3}$$

wherein $R_f$, R, o, p, and M are as defined above in Formula 1. Preferred compounds of Formula 3 include those wherein o and p are each 2, $R_f$ is $C_6H_{13}$, and R is $CH_2CH_2$. The fluoroalkyl alcohol used to prepare compounds of Formula 3 is available from E. I. du Pont de Nemours and Company, Wilmington Del. Alternatively the fluoroalkyl alcohol $R_f(CH_2)_oSO_2N(CH_3)(CH_2)_p$—OH, wherein o and p are defined above in Formula (1), is prepared by the reaction of a fluoroalkyl ethylene iodide with potassium thiocyanate in water. The product $R_f(CH_2)_oSCN$ is distilled as a colorless liquid, which then is converted to fluorinated sulfonyl chloride having the formula $R_f(CH_2)_oSO_2Cl$ by a reaction with chlorine and acetic acid over several hours at about 45~50° C. in an autoclave. The sulfonyl chloride is then reacted with an amine, for example, such as N-methylethanolamine, to produce the fluorinated alcohol of the formula $R_f(CH_2)_oSO_2N(CH_3)(CH_2)_p$—OH.

A further embodiment of the invention is a compound of Formula 1 wherein A is $O(CF_2)_q(CH_2)_r$—, herein denoted as Formula 4, $$R_f—O(CF_2)_q(CH_2)_r—OP(O)(O^-M^+)(OROH) \quad \text{Formula 4}$$

wherein $R_f$, R, q, r, and M are as defined above in Formula 1. Preferred compounds of Formula 4 include those wherein q and r are each 2, $R_f$ is $C_3F_7$, and R is $CH_2CH_2$.

The fluoroalcohols used as starting materials to make the compositions of Formula 4 are available by the following series of reactions of Scheme 2:

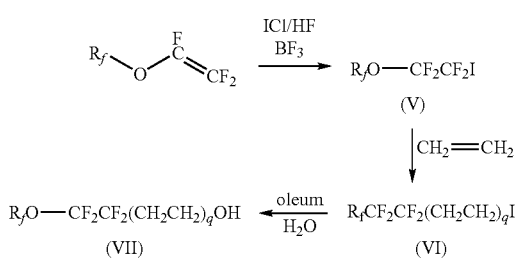

The starting perfluoroalkyl ether iodides of formula (V) in Scheme 2 can be made by the procedure described in U.S. Pat. No. 5,481,028, in Example 8, which discloses the preparation of compounds of formula (V) from perfluoro-n-propyl vinyl ether.

In the second reaction in Scheme 2, a perfluoroalkyl ether iodide (V) is reacted with an excess of ethylene at an elevated temperature and pressure. While the addition of ethylene can be carried out thermally, the use of a suitable initiator is preferred. Preferably the initiator is a peroxide such as benzoyl peroxide, isobutyryl peroxide, propionyl peroxide, or acetyl peroxide. More preferably the peroxide is benzoyl peroxide. The temperature of the reaction is not limited, but a temperature in the range of 110° C. to 130° C. is preferred. The reaction time can vary with the initiator and reaction conditions, but 24 hours is usually adequate. The product is purified by any means that separates unreacted starting material from the final product, but distillation is preferred. Satisfactory yields up to 80% of theory have been obtained using about 2.7 mols of ethylene per mole of perfluoalkyl ether iodide, a temperature of 110° C. and autogenous pressure, a reaction time of 24 hours, and purifying the product by distillation.

The perfluoroalkylether ethylene iodides (VI) in Scheme 2 are treated with oleum and hydrolyzed to provide the corresponding alcohols (VII) according to procedures disclosed in WO 95/11877 (Elf Atochem S.A.). Alternatively, the perfluoroalkylether ethyl iodides can be treated with N-methyl formamide followed by ethyl alcohol/acid hydrolysis. A temperature of about 130° to 160° C. is preferred. The higher homologs (q=2, 3) of telomer ethylene iodides (VI) in Scheme 2 are available with excess ethylene at high pressure.

The telomer ethylene iodides (VI) in Scheme 2 are treated with a variety of reagents to provide the corresponding thiols according to procedures described in J. Fluorine Chemistry, 104, 2 173-183 (2000). One example is the reaction of the telomer ethylene iodides (VI) of Scheme 2 with sodium thioacetate, followed by hydrolysis. The telomer ethylene iodide (VI) of Scheme 2 can also be treated to provide the corresponding thioethanols or thioethylamines by conventional methods.

A further embodiment of the invention is a compound of Formula 1 wherein A is OCHFCF$_2$OE-, herein denoted as Formula 5,

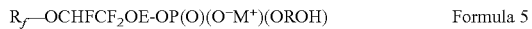

$R_f$—OCHFCF$_2$OE-OP(O)(O$^-$M$^+$)(OROH)          Formula 5 wherein $R_f$, R, E and M are as defined above in Formula 1. Preferred compounds of Formula 5 include those wherein $R_f$ is $C_3F_7$ and R is CH$_2$CH$_2$.

The fluoroalcohols used as starting materials to make the compositions of Formula 5 are prepared by reacting a dioxane with a diol in the presence of an alkali metal compound. For example a dioxane of formula $R_f$OCF=CF$_2$ is reacted with a diol such as HO(CH$_2$)OH in the presence of an alkali metal such as KOH typically in a sealed stainless steel reaction vessel at about 70° C. for about 8 hours. The diol is used at about 1 to about 15 mols per mol of ether, preferably from about 1 to about 5 mols per mol of ether. Suitable alkali metal compounds include an alkali metal, alkali earth metal, alkali hydroxide, alkali hydride, or an alkali amide. Preferred are alkali metals such as Na, K or Cs, or alkali hydrides such as NaH or KH. The reaction is conducted at a temperature of from about 40° C. to about 120° C. The reaction can be conducted in an optional solvent, such as ether or nitrile.

The compounds of the present invention of Formula 1 are surfactants for use in aqueous formulations, where extremely low surface tensions of about 18 dynes/cm or 18 mN/m (milli-newtons per meter) are required. The surfactants of the present invention provide "fluorine efficiency". The term "fluorine efficiency" means to increase the efficiency or improve the performance of the surfactants or treating agents so a lower proportion of the expensive fluorine component is required to achieve the same level of performance, or to have better performance using the same level of fluorine. Compared with conventional fluorinated surfactants, the fluorine content in the surfactants of the present invention is from about 50% to about 70% lower than in conventional fluorinated surfactants.

The above compound of Formula (1) is a fluorinated phosphate surfactant which lowers surface tension at very low concentration. Such surface tension values in a medium, typically a liquid are less than about 25 milli-newtons per meter, preferably less than about 20 milli-newtons per meter, at a concentration of the surfactant in the medium of less than about 0.2% by weight, and preferably less than 0.1% by weight. The surfactant is characterized by its efficiency in lowering the surface tension at low concentrations by selective adsorption on the interface, which is determined by the amphiphilic nature of the surfactants. The term "amphiphilic" means attraction to two different kinds of media. The surfactants comprise a water-soluble hydrophilic part and a water-insoluble hydrophobic part.

The present invention further comprises a method of lowering surface tension of an aqueous medium comprising contacting the medium with a composition of Formula 1 as described above. Any of a wide variety of media are suitable for use in the method of the present invention. Typically the medium is a liquid. Preferred are aqueous, hydrocarbon, and halocarbon systems. Examples of suitable medium include a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent. Adding a composition of the present invention to the medium results in lowering the surface tension of the medium due to the surfactant properties of the composition of the present invention. The composition of the present invention is typically simply blended with or added to the medium. A low concentration of about 0.1% by weight of surfactant is sufficient to lower surface tension to less than about 22 mN/m, preferably less than about 20 nM/m, more preferably less than about 18 mN/m.

The present invention further comprises a method of providing soil repellency, leveling, and resistance to blocking to a coated substrate comprising adding to a coating base prior to deposition on the substrate a compound of Formula 1. "Leveling" as used herein refers to the uniformity of coverage of the coating when applied to a substrate. It is undesirable to have streaking, surface defects, or withdrawal of the coating from the substrate surface at the edges or otherwise. An even coating will provide a superior dried coating on the substrate surface. "Blocking" is the undesirable sticking together of two coated surfaces when pressed together, or placed in contact with each other for an extended period of time, after the coating has dried. When blocking occurs separation of the surfaces can result in disruption of the coating on one or both surfaces. Thus resistance to blocking is beneficial in many situations where two coated surfaces need to be in contact, for example on window frames.

Suitable coating compositions, referred to herein by the term "coating base", include a composition, typically a liquid formulation, of an alkyd coating, Type I urethane coating, unsaturated polyester coating, or water-dispersed coating, and is applied to a substrate for the purpose of creating a lasting film on the substrate surface. These are conventional paints, stains, and similar coating compositions.

By the term "alkyd coating" as used herein is meant a conventional liquid coating based on alkyd resins, typically a paint, clear coating, or stain. The alkyd resins are complex branched and cross-linked polyesters containing unsaturated aliphatic acid residues. Conventional alkyd coatings utilize, as the binder or film-forming component, a curing or drying alkyd resin. Alkyd resin coatings contain unsaturated aliphatic acid residues derived from drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Such drying oils have been used as raw materials for oil-based coatings and are described in the literature.

By the term "urethane coating" as used hereinafter is meant a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. Urethane coatings are classified by ASTM D-1 into five categories. Type I urethane coatings contain a pre-reacted autoxidizable binder as described in Surface Coatings Vol. I, previously cited. These are also known as uralkyds, urethane-modified alkyds, oil-modified urethanes, urethane oils, or urethane alkyds, are the largest volume category of polyurethane coatings and include paints, clear coatings, or stains. The cured coating is formed by air oxidation and polymerization of the unsaturated drying oil residue in the binder.

By the term "unsaturated polyester coating" as used hereinafter is meant a conventional liquid coating based on unsaturated polyester resins, dissolved in monomers and containing initiators and catalysts as needed, typically as a paint, clear coating, or gel coat formulation. Unsaturated polyester resins contain as the unsaturated prepolymer the product obtained from the condensation polymerization of a glycol such as 1,2-propylene glycol or 1,3-butylene glycol with an unsaturated acid such as maleic (or of maleic and a saturated acid, e.g., phthalic) in the anhydride form. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. For curing coatings at room temperature, the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing using, for instance, ultraviolet light. This form of cure, in which no heat is produced, is particularly suited to films on wood or board. Other radiation sources, for instance electron-beam curing, are also used.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as well as members of other classifications. Water-dispersed coatings in general contain other common coating ingredients. Water-dispersed coatings are exemplified by, but not limited to, pigmented coatings such as latex paints, unpigmented coatings such as wood sealers, stains, and finishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

When used as additives to a coating base the compounds of the present invention of Formula 1 as defined above are effectively introduced to the coating base or other composition by thoroughly stirring it in at room or ambient temperature. More elaborate mixing can be employed such as using a mechanical shaker or providing heat or other methods. Such methods are not necessary and do not substantially improve the final composition. When used as an additive to latex paints, the compositions of the invention generally are added at about 0.001 weight % to about 5 weight % by dry weight of the composition of the invention in the wet paint. Preferably about from about 0.01 weight % to about 1 weight %, and more preferably from about 0.1 weight % to about 0.5 weight % is used.

Floor waxes, polishes, or finishes (hereinafter "floor finishes") are generally water based or solvent based polymer emulsions. The surfactants of Formula I of the present invention are suitable for use in such floor finishes. Commercially available floor finish compositions typically are aqueous emulsion-based polymer compositions comprising one or more organic solvents, plasticizers, coating aides, anti-foaming agents, surfactants, polymer emulsions, metal complexing agents, and waxes. The particle size range and solids content of the polymer are usually controlled to control the product viscosity, film hardness and resistance to deterioration. Polymers containing polar groups function to enhance solubility and may also act as wetting or leveling agents providing good optical properties such a high gloss and distinctness of reflected image.

Preferred polymers for use in floor finishes include acrylic polymers, polymers derived from cyclic ethers, and polymers derived from vinyl substituted aromatics. Acrylic polymers include various poly(alkyl acrylates), poly(alkyl methacrylates), hydroxyl substituted poly(alkyl acrylates) and poly (alkyl methacrylates). Commercially available acrylic copolymers used in floor finishes include, for example, methyl methacrylate/butyl acrylate/methacrylic acid (MMA/BA/MAA) copolymers; methyl methacrylate/butyl acrylate/acrylic acid (MMA/BA/AA) copolymers, and the like. Commercially available styrene-acrylic copolymers include styrene/methyl methacrylate/butyl acrylate/methacrylic acid (S/MMA/BA/MMA) copolymers; styrene/methyl methacrylate/butyl acrylate/acrylic acid (S/MMA/BA/AA) copolymers; and the like. Polymers derived from cyclic ethers usually contain 2 to 5 carbon atoms in the ring with optional alkyl groups substituted thereon. Examples include various oxiranes, oxetanes, tetrahydrofurans, tetrahydropyrans, dioxanes, trioxanes, and caprolactone. Polymers derived from vinyl substituted aromatics include for example those made from styrenes, pyridines, conjugated dienes, and copolymers thereof. Polyesters, polyamides, polyurethanes and polysiloxanes are also used in floor finishes.

The waxes or mixtures of waxes that are used in floor finishes include waxes of a vegetable, animal, synthetic, and/or mineral origin. Representative waxes include, for example, carnuba, candelilla, lanolin, stearin, beeswax, oxidized polyethylene wax, polyethylene emulsions, polypropylene, copolymers of ethylene and acrylic esters, hydrogenated coconut oil or soybean oil, and the mineral waxes such as paraffin or ceresin. The waxes typically range from 0 to about 15 weight percent and preferably from about 2 to about 10 weight percent based on the weight of the finish composition.

When used as additives to a floor finish the compositions of the present invention of Formula 1 as defined above are effectively introduced to the composition by thoroughly stirring it in at room or ambient temperature. More elaborate mixing can be employed such as using a mechanical shaker or providing heat or other methods. When used as an additive to floor finishes, the compositions of the invention generally are added at about 0.001 weight % to about 5 weight % by dry weight of the composition of the invention in the wet composition. Preferably about from about 0.01 weight % to about 1 weight %, and more preferably from about 0.1 weight % to about 0.5 weight % is used.

Floor waxes or polishes are water based, solvent based and polymer. The surfactants of the present invention are suitable for use with any of these. Water-based and polymer waxes dry to a high gloss without buffing; solvent-based wax requires vigorous buffing. Water-based wax is recommended for asphalt, vinyl, vinyl asbestos and rubber-tiled floors; solvent-based waxes produce a hard, shiny finish and are best for wood, cork and terrazzo floors. Self-polishing waxes, such as polymer or resin, will yellow or discolor and wear off in heavy traffic areas; they should be stripped off and reapplied after three or four coats.

The present invention further comprises a method of providing foaming in a medium comprising contacting the medium with a compound of Formula 1 as defined above. The compound of Formula 1 of the present invention is typically simply blended with or added to the medium. The surfactants of the present invention are stable in aqueous, brine, acidic and basic medium. When used as additives to provide foaming the compounds of the present invention of Formula 1 are effectively introduced to the medium by thoroughly stirring it in at room or ambient temperature. More elaborate mixing can be employed such as using a mechanical shaker, mechanical mixer, or providing heat or other methods. More vigorous stirring will typically produce a larger amount of foam. A low concentration of surfactant in the medium of a minimum of about 0.01% by weight, preferably 0.02% by weight, more preferably 0.1% is sufficient to provide foaming.

The surfactants used in the method of the present invention can both create foam and maintain a stable foam in aqueous solution over a period of time. The degree of foaming and the time a stable foam is maintained are useful in various applications. Foaming is an important property of fluorosurfactants that are used as additives for cleaners, drilling fluid additives for foaming, and fluid additives for oilfield stimulation activities. In cleaning solutions, foam is often used to promote adhesion of the active cleaning ingredient on the surface. The aqueous or solvent based drilling fluids foam during drilling and thus aid in the removal of fines from the well around the drill-bit. The addition of the fluorosurfactant boosts the drilling fluid foaming properties. If these fines are not efficiently removed, they can result in damage to the drill-bit head, costing time and money. The fluorosurfactants also boost properties of the stimulation fluids during well treatments, such as hydraulic fracture treatments or matrix treatments, performed to restore or enhance well productivity of oil and gas wells. The surfactants of Formula 1 and the method of providing foaming of the present invention are useful in these applications.

The surfactants of Formula 1 and the method of providing foaming of the present invention are also useful in applications requiring an aggressive (acidic or basic) medium. Examples of such applications include etching processes in the manufacture of electronic or photovoltaic components, or in aggressive cleaning solutions. For aggressive cleaners and etching applications, it is undesirable to have additives that create foams sustainable over a long time period. Such sustained foams require the use of defoamers during disposal and can create complications during manufacturing processes. Thus, providing foaming that is not maintained over a long time period, but instead disintegrates quickly in highly acidic and basic conditions, are desirable. The surfactants of Formula 1 and the method of providing foaming of the present invention provide foams that quickly disintegrate in aggressive medium. The foams provided by the method of the present invention disintegrate in about 15 minutes in acidic or basic medium, preferably in about 10 minutes, and more preferably in about 5 minutes. Thus, the surfactants of Formula 1 and the method of providing foaming of the present invention are useful in these applications.

Overall the surfactants of Formula 1 and the methods of the present invention are useful in a wide variety of end-use applications. The surfactants of the present invention provide compounds having surfactant effects at low concentrations, such as below 0.5% by weight in water. The compounds of the invention contain less fluorine (improved fluorine efficiency), have a lower surface tension or are generally comparable to conventional fluoroalkyl surfactants. The inventive compounds provide the advantage of altering surface properties, such as repellency, leveling, and resistance to blocking, using less fluorine to achieve the same level of performance, or provide better performance using the same level of fluorine, as prior art compositions. Thus the improvements in the surfactant characteristics reduce overall manufacturing cost while improving the performance of the surfactant products. The surfactants of the present invention also provide the advantage of stability in brine and aggressive media, such as acids and bases. This stability is unexpected for a phosphate functional surfactant. This stability means the surfactants are useful to provide surface activity and foaming properties in a variety of applications.

Materials and Test Methods

The following materials and test methods were used in the examples herein.

1) $C_6F_{13}CH_2CH_2OH$ available from Sigma Aldrich, St. Louis, Mo.

2) $C_4F_9CH_2CF_2CH_2CH_2OH$

Ethylene (25 g) was introduced to an autoclave charged with $C_4F_9CH_2CF_2I$ (217 g) and d-(+)-limonene (1 g), and the reactor heated at 240° C. for 12 h. The product was isolated by vacuum distillation to provide $C_4F_9CH_2CF_2CH_2CH_2I$. Fuming sulfuric acid (70 mL) was added slowly to 50 g of $C_4F_9CH_2CF_2CH_2CH_2I$ and mixture stirred at 60° C. for 1.5 h. The reaction was quenched with ice-cold 1.5 wt % $Na_2SO_3$ aqueous solution and heated at 95° C. for 0.5 h. The bottom layer was separated and washed with 10 wt % aqueous sodium acetate, and distilled to provide $C_4F_9CH_2CF_2CH_2CH_2OH$: bp 54~57° C. at 2 mmHg (267 Pascals).

3) $C_3F_7OCF_2CF_2CH_2CH_2OH$ $C_3F_7OCF_2CF_2I$ (100 g, 0.24 mol) and benzoyl peroxide (3 g) were charged under nitrogen into a vessel. A series of three vacuum/nitrogen gas sequences was then executed at –50° C. and ethylene (18 g, 0.64 mol) was introduced. The vessel was heated for 24 hour at 110° C. The autoclave was cooled to 0° C. and opened after degassing. Then the product was collected in a bottle. The product was distilled giving 80 g of $C_3F_7OCF_2CF_2CH_2CH_2I$ in 80% yield. The boiling point was 56~60° C. at 25 mm Hg pressure (3325 Pa).

A mixture of $C_3F_7OCF_2CF_2CH_2CH_2I$ (300 g, 0.68 mol) and N-methyl-formamide (300 mL), was heated to 150° C. for 26 hours. Then the reaction was cooled to 100° C., followed by the addition of water to separate the crude ester. Ethyl alcohol (77 mL) and p-toluene sulfonic acid (2.59 g) were added to the crude ester, and the reaction was stirred at 70° C. for 15 minutes. Then ethyl formate and ethyl alcohol were distilled out to give a crude product. The crude product was dissolved in ether, washed with aqueous sodium sulfite, water, and brine in turn, then dried over magnesium sulfate. The product was then distilled to give 199 g of $C_3F_7OCF_2CF_2CH_2CH_2OH$ in 85% yield. The boiling point was 71~73° C. at 40 mmHg (5320 Pa).

4) RHOPLEX 3829, formulation N-29-1 is available from Rohm & Haas, Philadelphia, Pa.

5) MAB paints are paints having an acrylic semi-gloss resin with 84% gloss at 85 degrees available from M. A. Bruder and Sons, Inc., Broomall, Pa.

6) TERGITOL 15-S-9 is available from Sigma Aldrich, St. Louis, Mo.

7) 1,3-Propanediol and poly(1,3-1,3-propanediol) are available from E. I. du Pont de Nemours and Company, Wilmington, Del.

8) Tetra(ethylene)glycol and poly(ethylene glycol) are available from Sigma Aldrich, St. Louis, Mo.

Test Method 1—Wetting and Leveling Test

To test the performance of the samples in their wetting and leveling ability, the samples were added to a floor polish (RHOPLEX 3829, Formulation N-29-1, available from Rohm & Haas, Philadelphia, Pa.]). Vinyl tiles, 12 inch by 12 inch (30.36 cm×30.36 cm) available from Interfuse Vinyl Tiles by Estrie, Sherbrooke, QC Canada, were thoroughly cleaned by wetting the tiles, adding a powdered oxygen bleach cleanser and scrubbing using a green SCOTCH-BRITE scouring pad, available from 3M Company, St. Paul, Minn. This scrubbing procedure was used to remove the pre-existing coating on the tiles. The tiles initially had a uniform shiny finish; a uniform dull finish indicated coating removal. The tiles were then air-dried overnight. A 1% by weight solution of the surfactant to be tested was prepared by dilution in deionized water. Following the resin manufacturer protocols, a 100 g portion of the RHOPLEX 3829 N-29-1 formulation was prepared, followed by addition of 0.75 g of the 1% by weight surfactant solution, to provide a test floor polish.

The test floor polish was applied to the tile by placing 3 mL portion of the test polish in the center of the tile, and spreading from top to bottom using a cheesecloth applicator, and finally placing a large "X" across the tile, using the applicator. The "X" subsequently provides visual evidence of leveling at the rating step. The applicator was prepared from a two-layer 18×36 inch (46×91 cm) sheet of cheesecloth (from VWR, West Chester Pa.), folded twice into an eight-layer pad. One corner of the pad was then used as the applicator. The tile was allowed to dry for 30 min. and a total of 5 coats (Coating #s 1-5) were applied and dried, with the X test performed after each coating had been dried. After each coat, the tile was rated on a 1 to 5 scale (1 being the worst, 5 the best) on the surfactant's ability to promote wetting and leveling of the polish on the tile surface. The rating is determined using the Tile Rating Scale below, based on comparison of a tile treated with the floor polish that contains no added surfactant.

TABLE 1

Visual Tile Rating Scale for Leveling

| Score | Description |
| --- | --- |
| 1 | Uneven surface coverage of the film, significant streaking and surface defects |
| 2 | Numerous surface defects and streaks are evident but, generally, film coats entire tile surface |
| 3 | Visible streaking and surface defects, withdrawal of the film from the edges of the tile |
| 4 | Minor surface imperfections or streaking |
| 5 | No visible surface defects or streaks |

Test Method 2—Surface Tension Measurement

Surface tension was measured according to the American Society for Testing and Materials ASTM #D1331-56, using the Wilhelmy plate method on a KRUSS K11 Version 2.501 tensiometer (KRUSS USA, Matthews N.C.) in accordance with instructions with the equipment. A vertical plate of known perimeter was attached to a balance, and the force due to wetting was measured. Each example to be tested was added to deionized water by weight based on solids of the additive in deionized water. Alternatively each example to be tested was added to 2% by weight KCl in deionized water, 15% by weight HCl in deionized water, or 15% by weight KOH in deionized water, each by weight based upon solids of the example in deionized water. Several different concentrations were prepared. Ten replicates were tested of each dilution, and the following machine settings were used:

Method: Plate Method SFT
Interval: 1.0 s
Wetted length: 40.2 mm

Reading limit: 10
Min Standard Deviation: 2 dynes/cm
Gr. Acc.: 9.80665 m/s$^2$
Results were in mN/m (dynes/cm) with a Standard Deviation of less than 1 dyne/cm. The tensiometer was used according to the manufacturer's recommendations.

Test Method 3—Contact Angle

Contact angles were measured by the Sessile Drop Method, which is described by A. W. Adamson in The Physical Chemistry of Surfaces, Fifth Edition, Wiley & Sons, New York, N.Y., 1990. Additional information on the equipment and procedure for measuring contact angles is provided by R. H. Dettre et al. in "Wettability", Ed. by J. C. Berg, Marcel Dekker, New York, N.Y., 1993.

In the Sessile Drop Method, a Ramè-Hart optical bench (available from Ramè-Hart Inc., 43 Bloomfield Ave., Mountain Lakes, N.J.) was used to hold the substrate in the horizontal position. The contact angle was measured at a prescribed temperature with a telescoping goniometer from the same manufacturer. Each Example to be tested was added to MAB paint at 0.018% by weight based on solids of the additive in the paint. A drop of test liquid was placed on a polyester scrub test panel (Leneta P-121 dull black or equivalent, Leneta Company, Mahwah, N.J.) and the tangent was precisely determined at the point of contact between the drop and the surface. An advancing angle was determined by increasing the size of the drop of liquid. The data were presented as advancing contact angles.

The relationship between organic liquid contact angles, and the cleanability and dirt retention of surfaces is described by A. W. Adamson, above. In general, higher hexadecane contact angles indicate that a surface has greater dirt and soil repellency, and easier surface cleanability.

Test Method 4—Blocking Resistance of Architectural Latex Paints

The test method described herein is a modification of ASTM D4946-89, Standard Test Method for Blocking Resistance of Architectural Paints, which is hereby specifically incorporated by reference. The face-to-face blocking resistance of paints to be tested was evaluated in this test. Blocking, for the purpose of this test, was defined as the undesirable sticking together of two painted surfaces when pressed together or placed in contact with each other for an extended period of time.

Each example to be tested was added to paint at 0.018% by weight based on solids of the additive in the paint. The paint used was MAB paint available from M.A. Bruder and Sons, Inc., Broomall, Pa. The paint to be tested was cast on a polyester test panel using an applicator blade. All painted panels were protected from surface contamination, such as grease, oil, fingerprints, dust, and the like. Typically, results were sought at 24 hours after casting the paint. After the panels had been conditioned in a conditioned room with controlled temperature and humidity as specified in the ASTM Test Method referenced above for the desired period of time, six squares (3.8 cm×3.8 cm) were cut out from the painted test panel. The cut sections (three pairs) were placed with the paint surfaces face-to-face for each of the paints to be tested. The face-to-face specimens were placed in a 50° C. oven on a marble tray. A no. 8 stopper was placed on top, with the smaller diameter in contact with the specimens, and then a 1000 g weight was placed on top of the stopper. This resulted in a pressure of 1.8 psi (12,400 Pascal) on the specimens. One weight and stopper was used for each specimen tested. After exactly 30 minutes, the stoppers and weights were taken off the test specimens which were removed from the oven and allowed to cool in the conditioned room for 30 minutes before determining the resistance to blocking.

After cooling, the specimens were separated by peeling apart with a slow and steady force. The blocking resistance was rated from 0 to 10, corresponding to a subjective tack assessment (sound made upon separation of the painted specimens) or seal (complete adhesion of the two painted surfaces) as determined by the operator of the method. The specimen was put near the ear to actually hear the degree of tack. The rating system is described in the Table 2 entitled Blocking Resistance Numerical Ratings below. The degree of seal was estimated from the appearance of the specimens and the fraction of the paint surfaces that adhere. Paint tearing away from the test panel backing was an indication of seal. A higher number indicated better resistance to blocking.

TABLE 2

Blocking Resistance Numerical Ratings

| Blocking Resistance Numerical Ratings | Description of the Separation | Performance Description |
|---|---|---|
| 10 | No tack | Perfect |
| 9 | Trace tack | Excellent |
| 8 | Very slight tack | Very good |
| 7 | Slight tack | Good/very good |
| 6 | Moderate to slight tack | Good |
| 5 | Moderate tack | Fair |
| 4 | Very tacky, no seal | Poor to Fair |
| 3 | 5-25% seal | Poor |
| 2 | 25-50% seal | Poor |
| 1 | 50-75% seal | Very poor |
| 0 | 75-100% seal | Very poor |

Test Method 5—Blender Foaming Test

The test procedure used to evaluate the foaming of fluorosurfactants for oilfield applications is a modified version of the blender foaming test ASTM D3519-88—Standard Test Method for Foam in Aqueous Media (Blender Test). The ability of the samples to create foam and maintain stable foam in aqueous solution over a period of time was evaluated in this test. A blender, graduated cylinder, glass sample bottles and a stop watch were the only materials required. First, stock solutions of the testing base solutions were made. These solutions were hard water, tap water, deionized water, or artificial sea water. Samples of 100 mL of the fluorosurfactant to be tested at 0.1% active ingredient in the desired base testing solution were prepared and stirred overnight to ensure complete mixing. The blender was cleaned with copious amounts of deionized water. Once clean, the blender was assembled for use. The test fluid sample of 100 mL was poured into the blender jar. The temperature of the test fluid was measured with a thermometer and recorded. The blender was then run for 20 seconds at 50-60% power. After 20 seconds, the liquid and foam were immediately poured into a 500 mL graduated cylinder. The initial liquid and foam height were measured in mL and a timer was started. This was designated the maximum total foam height at time zero. The graduated cylinder was allowed to stand undisturbed. Additional liquid and foam height (in mL) measurements were taken 5, 10 and 15 minutes after the stop watch was started. In addition, the half-life of the foam was also recorded. The half-life was the time when half of the liquid had drained to the bottom of the graduated cylinder. During this time, any observations of the foam were recorded such as dense or thin foam and foam persistency. A larger height (in mL) of the foam indicated that the sample foamed more. A consistently high height (in mL) of foam demonstrated persistent foam. The blender foaming test was used as an indicator of the amount of foam that a sample produced and also displayed the persistence of that foam.

Test Method 6—Nitrogen Bubbling Foam Test

The nitrogen bubbling foam test procedure was used to evaluate the foaming of fluorosurfactants in acidic and basic solutions for cleaning and etching application. First, stock solutions of the testing base solutions were made. These solutions were 15% HCl and 15% KOH. Samples of 20 mL of the fluorosurfactant to be tested at 0.1% active ingredient in the desired base testing solution were prepared and stirred overnight to ensure complete mixing. The sample solution was then added to a 100 mL graduated cylinder (glass). Nitrogen was then bubbled through the solution to produce foam at a rate that filled the cylinder in 20-30 seconds. A fritted glass tube was used to bubble the nitrogen through the solution. When the foam reached the top of the cylinder, the nitrogen was turned off and a timer was started. The heights of the foam and liquid in mL were measured after 30 seconds, 5 minutes, 10 minutes, and 15 minutes. Observations of the quality and persistency of the foam were also recorded. The nitrogen bubbling foam test was used as an indicator of the amount of foam that a sample produced and the persistency of that foam.

Test Method 7—Wickbold Torch Method (for Fluorine Analyses)

An efficient process for the quantitative mineralization of fluorinated compounds is the Wickbold torch combustion method. The method (described in detail in Angew Chem. 66 (1954) 173) was demonstrated to be compound independent for fluorine-containing compounds. In this process, the analytical sample was placed in a ceramic vessel and the sample, typically, was completely combusted by external heating in a vigorous oxygen stream. The gaseous reaction products wee passed through an auxiliary hydrogen/oxygen flame with excess oxygen, so the combustion became complete. The gaseous effluent was then condensed, and fluoride was solubilized in the aqueous stream which was collected for analysis. The aqueous fluoride was then easily measured, typically using a fluoride ion selective electrode.

EXAMPLES

Example 1

Phosphorus pentoxide (2.52 g, 0.018 mol) was added to $C_6F_{13}CH_2CH_2OH$ (5 g, 0.014 mol) at 80° C. and the reaction was heated to 105° C. for 6 hours. Propanediol (3.14 g, 0.041 mol) was added to the reaction mixture at 95° C., stirred for 3.5 hours, followed by the addition of TERGITOL 15-S-9 surfactant, available from Sigma Aldrich, St. Louis, Mo., (2.11 g) at 86° C. After 10 min, ammonia (2.49 mL, 0.04 mol, 30%) was added and the reaction was stirred for 10 min at 70° C. Water (77.5 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 2

Phosphorus pentoxide (1.51 g, 0.011 mol) was added to $C_6F_{13}CH_2CH_2OH$ (2 g, 0.0055 mol) at 80° C. and the reaction was heated to 105° C. for 6 hours. Propanediol (2.09 g, 0.0275 mol) was added to the reaction mixture at 95° C., stirred for 3.5 hours, followed by the addition of TERGITOL 15-S-9 surfactant, available from Sigma Aldrich, St. Louis, Mo., (1.26 g) at 86° C. After 10 min, ammonia (1.49 mL, 0.024 mol, 30%) was added and the reaction was stirred for 10 min at 70° C. Water (46.5 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 3

Phosphorus pentoxide (1.51 g, 0.011 mol) was added to $C_6F_{13}CH_2CH_2OH$ (4 g, 0.011 mol) at 80° C. and the reaction was heated to 105° C. for 12 hours. Polyethylene glycol (MW 200: 4.4 g, 0.022 mol) was added to the reaction mixture at 100° C. and stirred for 12 hours, followed by the addition of TERGITOL 15-S-9 surfactant, available from Sigma Aldrich, St. Louis, Mo., (1.37 g) at 86° C. After 10 min, ammonia (1.49 mL, 0.024 mol, 30%) was added and the reaction was stirred for 10 min at 70° C. Water (46.5 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 4

Phosphorus pentoxide (1.33 g, 0.0096 mol) was added to $C_6F_{13}CH_2CH_2OH$ (3.5 g, 0.0096 mol) at 80° C. and the reaction was heated to 105° C. for 12 hours. Polyethylene glycol (MW 300: 5.77 g, 0.019 mol) was added to the reaction mixture at 95° C. and stirred for 12 hours, followed by the addition of TERGITOL 15-S-9 surfactant, available from Sigma Aldrich, St. Louis, Mo., (1.24 g) at 86° C. After 10 min, ammonia (1.31 mL, 0.021 mol, 30%) was added and the reaction was stirred for 10 min at 70° C. Water (46.7 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6. The product was also tested for surface tension in 2% KCl, 15% HCl, and 15% KOH according to Test Method 2. The results are listed in Tables 7 to 9. In addition the product was tested for foaming using Test Methods 5 and 6. The results are in Tables 10 to 12.

Example 5

Phosphorus pentoxide (1.26 g, 0.0092 mol) was added to $C_6F_{13}CH_2CH_2OH$ (4 g, 0.011 mol) at 80° C. and the reaction was heated to 105° C. for 12 hours. Polyethylene glycol (MW 400: 6.59 g, 0.016 mol) was added to the reaction mixture at 100° C. and stirred for 12 hours, followed by the addition of TERGITOL 15-S-9 surfactant, available from Sigma Aldrich, St. Louis, Mo., (1.22 g) at 86° C. After 10 min, ammonia (1.24 mL, 0.020 mol, 30%) was added and the reaction was stirred for 10 min at 70° C. Water (38.8 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6. The product was also tested for surface tension in 2% KCl, 15% HCl, and 15% KOH according to Test Method 2. The results are listed in Tables 7 to 9. In addition the product was tested for foaming using Test Methods 5 and 6. The results are in Tables 10 to 12.

Example 6

Phosphorus pentoxide (1.01 g, 0.0073 mol) was added to $C_6F_{13}CH_2CH_2OH$ (4 g, 0.011 mol) at 80° C. and the reaction was heated to 105° C. for 12 hours. Polyethylene glycol (MW 600: 6.59 g, 0.011 mol) was added to the reaction mixture at 100° C. and stirred for 12 hours, followed by the addition of TERGITOL 15-S-9 surfactant, available from Sigma Aldrich, St. Louis, Mo., (1.03 g) at 86° C. After 10 min, ammonia (1.0 mL, 0.016 mol, 30%) was added and the reaction was stirred for 10 min at 70° C. Water (31 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6. The product was also tested for surface tension in 2% KCl, 15% HCl, and 15% KOH according to Test Method 2. The results are listed in Tables 7 to 9. In addition the product was tested for foaming using Test Methods 5 and 6. The results are in Tables 10 to 12.

Example 7

Phosphorus pentoxide (1.58 g, 0.011 mol) was added to $C_6F_{13}CH_2CH_2OH$ (5 g, 0.014 mol) at 80° C. and the reaction was heated to 105° C. for 12 hours. Polypropylene diol (MW 250: 5.15 g, 0.021 mol) was added to the reaction mixture at 100° C. and stirred for 12 hours, followed by the addition of TERGITOL 15-S-9 surfactant, available from Sigma Aldrich, St. Louis, Mo., (1.46 g) at 86° C. After 10 min, ammonia (1.56 mL, 0.025 mol, 30%) was added and the reaction was stirred for 10 min at 70° C. Water (48.5 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 8

Phosphorus pentoxide (1.18 g, 0.0086 mol) was added to $C_6F_{13}CH_2CH_2OH$ (5 g, 0.014 mol) at 80° C. and the reaction was heated to 105° C. for 12 hours. Polypropylene diol (MW 650: 7.82 g, 0.0086 mol) was added to the reaction mixture at 100° C. and stirred for 12 hours, followed by the addition of TERGITOL 15-S-9 surfactant, available from Sigma Aldrich, St. Louis, Mo., (1.21 g) at 86° C. After 10 min, ammonia (1.17 mL, 0.019 mol, 30%) was added and the reaction was stirred for 10 min at 70° C. Water (36.3 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 9

Phosphorus pentoxide (1.08 g, 0.0076 mol) was added to $C_4F_9CH_2CF_2CH_2CH_2OH$ (2.5 g, 0.0076 mol) at 80° C. and the reaction was heated to 105° C. for 6 hours. Propanediol (1.16 g, 0.015 mol) was added to the reaction mixture at 95° C., stirred overnight, followed by the addition of TERGITOL 15-S-9 surfactant, available from Sigma Aldrich, St. Louis, Mo., (0.90 g) at 86° C. After 10 min, ammonia (1.04 mL, 0.017 mol, 30%) was added and the reaction was stirred for 10 min at 70° C. Water (32 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 10

Phosphorus pentoxide (1.08 g, 0.0076 mol) was added to $C_3F_7OC_2F_4CH_2CH_2OH$ (2.5 g, 0.0076 mol) at 80° C. and the reaction was heated to 105° C. for 6 hours. Propanediol (1.15 g, 0.015 mol) was added to the reaction mixture at 95° C., stirred for overnight, followed by the addition of TERGITOL 15-S-9 surfactant, available from Sigma Aldrich, St. Louis, Mo., (0.89 g) at 86° C. After 10 min, ammonia (0.94 mL, 0.017 mol, 30%) was added and the reaction was stirred for 10 min at 70° C. Water (32 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 11

Phosphorus pentoxide (0.77 g, 0.0054 mol) was added to $C_4F_9CH_2CF_2CH_2CH_2OH$ (2.5 g, 0.0076 mol) at 80° C. and the reaction was heated to 105° C. for 12 hours. Polypropylene diol (MW 250: 2.16 g, 0.0086 mol) was added to the reaction mixture at 100° C. and stirred for 12 hours, followed by the addition of TERGITOL 15-S-9 surfactant, available from Sigma Aldrich, St. Louis, Mo., (0.69 g) at 86° C. After 10 min, ammonia (0.73 mL, 0.012 mol, 30%) was added and the reaction was stirred for 10 min at 70° C. Water (23 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 12

Phosphorus pentoxide (0.77 g, 0.0054 mol) was added to $C_3F_7OC_2F_4CH_2CH_2OH$ (2.5 g, 0.0076 mol) at 80° C. and the reaction was heated to 105° C. for 12 hours. Polypropylene diol (MW 250: 2.16 g, 0.0086 mol) was added to the reaction mixture at 100° C. and stirred for 12 hours, followed by the addition of TERGITOL 15-S-9 surfactant, available from Sigma Aldrich, St. Louis, Mo., (0.67 g) at 86° C. After 10 min, ammonia (0.73 mL, 0.012 mol, 30%) was added and the reaction was stirred for 10 min at 70° C. Water (23 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 13

Phosphorus pentoxide (0.72 g, 0.0051 mol) was added to $C_4F_9CH_2CF_2CH_2CH_2OH$ (2.5 g, 0.0076 mol) at 80° C. and the reaction was heated to 105° C. for 12 hours. Polyethylene glycol (MW 600: 4.57 g, 0.0076 mol) was added to the reaction mixture at 95° C., stirred overnight, followed by the addition of TERGITOL 15-S-9 surfactant, available from Sigma Aldrich, St. Louis, Mo., (0.71 g) at 86° C. After 10 min, ammonia (0.69 mL, 0.011 mol, 30%) was added and the reaction was stirred for 10 min at 70° C. Water (31 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 14

Phosphorus pentoxide (0.72 g, 0.005 mol) was added to $C_3F_7OC_2F_4CH_2CH_2OH$ (2.5 g, 0.0076 mol) at 80° C. and the reaction was heated to 105° C. for 12 hours. Polyethylene glycol (MW 600: 4.57 g, 0.0076 mol) was added to the reaction mixture at 95° C., stirred for overnight, followed by the addition of TERGITOL 15-S-9 surfactant, available from Sigma Aldrich, St. Louis, Mo., (0.70 g) at 86° C. After 10 min, ammonia (0.69 mL, 0.011 mol, 30%) was added and the reaction was stirred for 10 min at 70° C. Water (30 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 15

Phosphorus pentoxide (1.26 g, 0.0092 mol) was added to $C_6F_{13}CH_2CH_2OH$ (2.5 g, 0.0067 mol) at 80° C. and the reaction was heated to 105° C. for 12 hours. Tetra(ethylene) glycol (3.67 g, 0.019 mol) was added to the reaction mixture at 100° C. and stirred for 12 hours, followed by the addition of TERGITOL 15-S-9 surfactant, available from Sigma Aldrich, St. Louis, Mo., (1.06 g) at 86° C. After 10 min, ammonia (1.17 mL, 0.019 mol, 30%) was added and the reaction was stirred for 10 min at 70° C. Water (36 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 16

Phosphorus pentoxide (1.26 g, 0.0092 mol) was added to $C_6F_{13}CH_2CH_2OH$ (2.5 g, 0.0067 mol) at 80° C. and the reaction was heated to 105° C. for 12 hours. Tetra(ethylene) glycol (4.27 g, 0.022 mol) was added to the reaction mixture at 100° C. and stirred for 12 hours, followed by the addition of TERGITOL 15-S-9 surfactant, available from Sigma Aldrich, St. Louis, Mo., (1.12 g) at 86° C. After 10 min, ammonia (1.24 mL, 0.2 mol, 30%) was added and the reaction was stirred for 10 min at 70° C. Water (39 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 17

Phosphorus pentoxide (1.26 g, 0.0092 mol) was added to $C_4F_9CH_2CF_2CH_2CH_2OH$ (2.5 g, 0.0076 mol) at 80° C. and the reaction was heated to 105° C. for 12 hours. Tetra(ethylene)glycol (4.07 g, 0.021 mol) was added to the reaction mixture at 100° C. and stirred for 12 hours, followed by the addition of TERGITOL 15-S-9 surfactant, available from Sigma Aldrich, St. Louis, Mo., (1.17 g) at 86° C. After 10 min, ammonia (1.29 mL, 0.021 mol, 30%) was added and the reaction was stirred for 10 min at 70° C. Water (40 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Example 18

Phosphorus pentoxide (1.34 g, 0.0092 mol) was added to $C_3F_7OC_2F_4CH_2CH_2OH$ (2.5 g, 0.0077 mol) at 80° C. and the reaction was heated to 105° C. for 12 hours. Tetra(ethylene) glycol (4.05 g, 0.021 mol) was added to the reaction mixture at 100° C. and stirred for 12 hours, followed by the addition of TERGITOL 15-S-9 surfactant, available from Sigma Aldrich, St. Louis, Mo., (1.16 g) at 86° C. After 10 min, ammonia (1.29 mL, 0.021 mol, 30%) was added and the reaction was stirred for 10 min at 70° C. Water (40 mL) was added and the reaction was stirred at 70° C. for 1 h to provide a phosphate of Formula 1. The resulting product was tested for leveling, surface tension, contact angle, and resistance to blocking using Test Methods 1 to 4. The results are listed in Tables 3 to 6.

Comparative Example A

Phosphorus pentoxide (1 equivalent) was added to a perfluoroalkylethyl alcohol mixture of the formula $F(CF_2)_a CH_2CH_2OH$ (2.3 equivalents). at 80° C. The typical mixture was as follows: 1.6% of a=4, 48.3% of a=6, 28.7% of a=8, 13.9% of a=10, 5.3% of a=12, 1.7 of a=14, 0.4% of a=16 and 0.1% of a=18. The reaction was heated to 105° C. for 24 hours. Ammonia (30% solution in water, 2.6 equivalents) was added and the reaction was stirred for 10 min. at 70° C. Water was added and the reaction was stirred at 70° C. for 1 hour to provide a phosphate product. The resulting product was tested for leveling, surface tension, contact angle, and resistance to blocking using Test Methods 1 to 4. The results are listed in Tables 3 to 6.

TABLE 3

Surface Tension in Deionized Water, dynes/cm (mN/m)

| | Concentration, % by weight | | | | |
| --- | --- | --- | --- | --- | --- |
| Example | 0.000% | 0.001% | 0.010% | 0.100% | 0.500% |
| 1 | 73.4 | 62.8 | 23.5 | 17.6 | 16.5 |
| 2 | 72.6 | 59.1 | 32.9 | 18.0 | 16.6 |
| 3 | 72.8 | 59.8 | 21.8 | 17.4 | 16.4 |
| 4 | 73.2 | 65.9 | 24.4 | 18.9 | 16.3 |
| 5 | 72.4 | 61.5 | 25.5 | 17.4 | 16.9 |
| 6 | 71.6 | 60.4 | 25.1 | 16.9 | 16.5 |
| 7 | 72.3 | 60.8 | 21.7 | 17.9 | 16.8 |
| 8 | 72.3 | 62.1 | 22.7 | 16.9 | 16.6 |
| 9 | 72.6 | 48.3 | 25.9 | 17.3 | 17.0 |
| 10 | 72.7 | 48.6 | 23.0 | 17.9 | 17.2 |
| 11 | 72.4 | 55.2 | 17.2 | 17.7 | 17.5 |
| 12 | 72.4 | 49.2 | 24.1 | 17.4 | 16.9 |
| 13 | 72.3 | 60.2 | 28.5 | 20.3 | 17.0 |
| 14 | 72.4 | 60.0 | 23.9 | 17.7 | 17.1 |
| 15 | 72.3 | 64.3 | 39.8 | 17.9 | 17.2 |
| 16 | 72.6 | 63.4 | 41.5 | 19.1 | 18.2 |
| 17 | 72.8 | 58.8 | 27.7 | 20.5 | 17.7 |
| 18 | 72.3 | 55.9 | 24.6 | 17.7 | 17.6 |
| Comparative A | 73.4 | 73.1 | 55.8 | 43.8 | 29.0 |

Normal surface tension of deionized water is 72 dyne/cm (mN/m) which is shown in Table 3 as 0.000% concentration of the surfactant in deionized water. When the phosphates of the present invention of Examples 1 to 18 were each added at a specified concentration, the surface tension of each aqueous solution was reduced significantly. Better performance was obtained at higher levels. According to the results from the test, excellent surface tension reduction was seen from the present invention. The surface tension reduction was superior to Comparative Example A despite the Examples containing less fluorine.

TABLE 4

Resistance to Blocking in Paint

| Example | Blocking Rating* | Fluorine (ppm)** |
|---|---|---|
| Control | 0 | 0 |
| 1 | 9.0 | 54 |
| 2 | 8.7 | 42 |
| 3 | 8.7 | 48 |
| 4 | 8.3 | 40 |
| 5 | 8.0 | 40 |
| 6 | 8.0 | 42 |
| 7 | 8.7 | 48 |
| 8 | 8.0 | 49 |
| 9 | 8.3 | 60 |
| 10 | 8.3 | 60 |
| 11 | 7.3 | 53 |
| 12 | 8.3 | 58 |
| 13 | 7.0 | 37 |
| 14 | 8.3 | 37 |
| 15 | 9.0 | 41 |
| 16 | 8.0 | 32 |
| 17 | 7.0 | 36 |
| 18 | 8.7 | 36 |
| Comparative A | 7.3 | 110 |

*Average of 3 replicates
**ppm is micrograms per gram

The data in Table 4 demonstrates that excellent resistance to blocking was obtained from the Examples 1 to 18 of the present invention compared to Comparative Example A, while the Examples 1 to 18 had much lower fluorine content.

TABLE 5

Leveling in RHOPLEX Floor Finish

| Examples | Reading* | F (ppm**) |
|---|---|---|
| Blank | 1.2 | 0 |
| 1 | 3.3 | 23 |
| 2 | 3.6 | 18 |
| 3 | 4 | 20 |
| 4 | 3.4 | 17 |
| 5 | 3.4 | 16 |
| 6 | 3.4 | 18 |
| 7 | 3.3 | 20 |
| 8 | 3.6 | 21 |
| 9 | 3.4 | 25 |
| 10 | 4 | 25 |
| 11 | 3.3 | 22 |
| 12 | 3.5 | 24 |
| 13 | 3.2 | 15 |
| 14 | 3.4 | 15 |
| 15 | 3.1 | 17 |
| 16 | 3 | 14 |
| 17 | 2.9 | 15 |
| 18 | 2.9 | 15 |
| Comparative A | 3.5 | 49 |

*Average of 5 coats
**ppm is micrograms per gram

The phosphates of Examples 1 to 18 exhibited excellent wetting ability in a floor finish (RHOPLEX) formulation. They performed equally to or better than Comparative Example A comprising fluorinated phosphate having a higher fluorine content when tested on vinyl tile.

TABLE 6

Advancing Contact Angle in Paint

| Example | Hexadecane | F (ppm*) |
|---|---|---|
| Control | 0 | 0 |
| 1 | 79.7 | 54 |
| 2 | 80.9 | 42 |
| 3 | 79.2 | 48 |
| 4 | 81.4 | 40 |
| 5 | 79.8 | 40 |
| 6 | 81.4 | 42 |
| 7 | 81.8 | 48 |
| 8 | 78.8 | 49 |
| 9 | 75.2 | 60 |
| 10 | 75.6 | 60 |
| 11 | 74.4 | 53 |
| 12 | 75.3 | 58 |
| 13 | 70.6 | 37 |
| 14 | 75.2 | 37 |
| 15 | 81.1 | 41 |
| 16 | 80.3 | 32 |
| 17 | 69.9 | 36 |
| 18 | 76.5 | 36 |
| Comparative A | 75.9 | 110 |

**ppm is micrograms per gram

The data in Table 6 showed excellent increased hexadecane contact angle for Examples 1 to 18 of the present invention compared to the control. The increase in the advancing hexadecane contact angle correlated with improved soil repellency. The present invention also performed equally to or better than the Comparative Example A at significant lower levels of fluorine.

TABLE 7

Surface Tension in 2% KCl, dynes/cm (mN/m)

| | Concentration, % by weight | | | | |
|---|---|---|---|---|---|
| Example | 0.000% | 0.001% | 0.010% | 0.100% | 0.500% |
| 4 | 74.0 | 58.9 | 39.0 | 25.9 | 19.9 |
| 5 | 74.0 | 57.1 | 39.8 | 26.6 | 21.2 |
| 6 | 74.1 | 58.1 | 36.6 | 27.4 | 20.6 |
| Comparative A | 74.0 | 69.4 | 51.7 | 33.3 | 30.0 |

TABLE 8

Surface Tension in 15% HCl, dynes/cm (mN/m)

| | Concentration, % by weight | | | | |
|---|---|---|---|---|---|
| Example | 0.000% | 0.001% | 0.010% | 0.100% | 0.500% |
| 4 | 72.6 | 49.3 | 22.1 | 20.5 | 20.2 |
| 5 | 72.7 | 45.3 | 22.0 | 21.4 | 21.1 |
| 6 | 72.8 | 43.3 | 23.0 | 20.9 | 20.7 |
| Comparative A | 72.6 | N/A | N/A | N/A | N/A |

TABLE 9

Surface Tension in 15% KOH, dynes/cm (mN/m)

| | Concentration, % by weight | | | | |
|---|---|---|---|---|---|
| Example | 0.000% | 0.001% | 0.010% | 0.100% | 0.500% |
| 4 | 82.3 | 59.4 | 31.3 | 27.7 | 26.0 |
| 5 | 82.3 | 55.5 | 32.3 | 27.6 | 26.4 |
| 6 | 81.7 | 60.5 | 35.8 | 28.2 | 25.7 |
| Comparative A | 82.0 | N/A | N/A | N/A | N/A |

Normal surface tension of each of 2% KCl, 15% HCl, and 15% KOH in deionized water is 74 dyne/cm (mN/m). This is shown in Tables 7 to 9 as 0.000% concentration. When the Examples 4 to 6 were each added at a specified rate, the surface tension of each aqueous solution was reduced significantly. Better performance was obtained at higher levels. According to the results from the test, excellent surface tension reduction was seen from the present invention. The surface tension results in 2% KCl of Examples 4, 5, and 6 demonstrated the improved surface active capability over the Comparative Example A. The Comparative Example A was not stable in 15% KCl and 15% KOH, and thus no surface tension measurements could be taken.

TABLE 10

Blender Foaming in Deionized Water

| Example | Foam Volume (mL) | | | |
|---|---|---|---|---|
|  | Initial | t = 5 min | t = 10 min | t = 15 min |
| 4 | 175 | 56 | 35 | 28 |
| 5 | 180 | 72 | 41 | 30 |
| 6 | 175 | 54 | 37 | 32 |
| Comparative A | 10 | 6 | 5 | 4 |

TABLE 11

Blender Foaming in 10% NaCl

| Example | Foam Volume (mL) | | | |
|---|---|---|---|---|
|  | Initial | t = 5 min | t = 10 min | t = 15 min |
| 4 | 175 | 79 | 77 | 77 |
| 5 | 150 | 48 | 46 | 41 |
| 6 | 180 | 74 | 67 | 62 |
| Comparative A* | N/A | N/A | N/A | N/A |

*The Comparative Example A was not stable in 10% NaCl and thus the blender foaming test could not be conducted.

The blender foaming results in deionized water and 10% NaCl shown in Tables 10 and 11, respectively, demonstrated improved foaming and a more sustainable foam with time over Comparative Example A. Foaming properties are desirable for cleaning solutions where the foam is used to promote adhesion of the active cleaning ingredient on the surface. In oilfield stimulation and drilling applications surfactant additives that help boost the foaming properties of the fluids are desirable.

TABLE 12

Nitrogen Bubble Foaming in 15% HCl

| Example* | Foam Volume (mL) | | | |
|---|---|---|---|---|
|  | Initial | t = 5 min | t = 10 min | t = 15 min |
| 4 | 34 | 11 | 6 | 6 |
| 5 | 52 | 26 | 11 | 11 |
| 6 | 99 | 51 | 46 | 44 |
| Comparative A* | N/A | N/A | N/A | N/A |

*The Comparative Example A was not stable in 15% HCl and thus the blender foaming test could not be conducted.

TABLE 13

Nitrogen Bubble Foaming in 15% KOH

| Example | Foam Volume (mL) | | | |
|---|---|---|---|---|
|  | Initial | t = 5 min | t = 10 min | t = 15 min |
| 4 | 112 | 56 | 46 | 31 |
| 5 | 113 | 41 | 21 | 16 |
| 6 | 96 | 39 | 31 | 24 |
| Comparative A* | N/A | N/A | N/A | N/A |

*The Comparative Example A was not stable in 15% KOH and thus the blender foaming test could not be conducted.

The nitrogen bubble foaming results in 15% HCl and in 15% KOH in Tables 12 and 13 respectively demonstrated a level of foaming and disintegration of foam that is desirable for aggressive (acid and base) cleaners and etching applications. The stability of Examples 4, 5 and 6 in 15% HCl and 15% KOH was superior to Comparative Example A.

What is claimed is:

1. A compound of Formula 1

$$R_f\text{-A-OP(O)(O}^-\text{M}^+)(\text{OROH})$$ <span style="float:right">Formula 1</span> wherein
$R_f$ is a $C_2$ to $C_6$ linear or branched perfluoroalkyl optionally interrupted by one, two or three ether oxygen atoms;

A is $(CH_2CF_2)_m(CH_2)_n$—, $(CH_2)_oSO_2N(CH_3)(CH_2)_p$—, $O(CF_2)_q(CH_2)_r$—, or $OCHFCF_2OE$-; 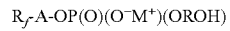

m is 0 to 4; n, o, p, and r are each independently 2 to 20; q is 2;

E is a $C_2$ to $C_{20}$ linear or branched alkyl group optionally interrupted by oxygen, sulfur, or nitrogen atoms; a cyclic alkyl group, or a $C_6$ to $C_{10}$ aryl group;

M is H or a Group I metal or an ammonium cation $(NH_xR^2_y)^+$ wherein $R^2$ is a $C_1$ to $C_4$ alkyl, x is 0 to 4, y is 0 to 4 and x+y is 4; and R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2.

2. The compound of claim 1 wherein R is a $C_2$ to $C_8$ linear or branched alkyl.

3. The compound of claim 1 wherein R is a $C_8$ to $C_{40}$ linear or branched alkyl interrupted by from about 2 to about 20 oxygen atoms, wherein the ratio of oxygen atoms to carbon atoms is from about 1:2 to about 1:4.

4. The compound of claim 1 wherein M is H, sodium, potassium, or an ammonium cation $(NH_xR^2_y)^+$ wherein $R^2$ is a $C_1$ to $C_4$ alkyl, x is 0 to 4, y is 0 to 4 and x+y is 4.

5. The compound of claim 1 wherein A is $(CH_2CF_2)_m$ $(CH_2)_n$—; m=0, 1, or 2; n is 2; $R_f$ is $C_4F_9$ or $C_6F_{13}$; and R is a $C_3$ alkyl or a $C_8$ to $C_{40}$ linear or branched alkyl interrupted by from about 2 to about 20 oxygen atoms.

6. The compound of claim 1 wherein A is $(CH_2)_oSO_2N$ $(CH_3)(CH_2)_p$—, o and p are each 2, $R_f$ is $C_4F_9$ or $C_6F_{13}$, and R is a $C_3$ alkyl or a $C_8$ to $C_{40}$ linear or branched alkyl interrupted by from about 2 to about 20 oxygen atoms.

7. The compound of claim 1 wherein A is $O(CF_2)_q(CH_2)_r$ —, q and r are each 2, $R_f$ is $C_2F_5$ or $C_3F_7$, and R is a $C_3$ alkyl or a $C_8$ to $C_{40}$ linear or branched alkyl interrupted by from about 2 to about 20 oxygen atoms.

8. The compound of claim 1 wherein A is $OCHFCF_2OE$-, $R_f$ is $C_2F_5$ or $C_3F_7$, and R is a $C_3$ alkyl or a $C_8$ to $C_{40}$ linear or branched alkyl interrupted by from about 2 to about 20 oxygen atoms.

9. The compound of claim 1 having a surface tension of about 22 mN/m or less at a concentration of 0.1% by weight in water.

10. The compound of claim 1 having a surface tension of about 18 mN/m or less at a concentration of 0.5% by weight in water.

11. A method of lowering the surface tension of an aqueous medium comprising contacting the medium with a composition of Formula 1

$R_f$-A-OP(O)(O$^-$M$^+$)(OROH)  Formula 1 wherein
- $R_f$ is a $C_2$ to $C_6$ linear or branched perfluoroalkyl optionally interrupted by one, two or three ether oxygen atoms;
- A is $(CH_2CF_2)_m(CH_2)_n$—, $(CH_2)_oSO_2N(CH_3)(CH_2)_p$—, $O(CF_2)_q(CH_2)_r$—, or $OCHFCF_2OE$-;
- m is 0 to 4; n, o, p, and r are each independently 2 to 20; q is 2;
- E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
- M is H or a Group I metal or an ammonium cation $(NH_xR^2_y)^+$ wherein $R^2$ is a $C_1$ to $C_4$ alkyl, x is 0 to 4, y is 0 to 4 and x+y is 4; and
- R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2.

12. The method of claim 11 wherein the medium is a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent.

13. The method of claim 11 wherein the compound of Formula 1 is applied to a substrate prior to contacting with the medium.

14. The method of claim 11 wherein the medium is an acid, base, or brine.

15. A method of providing soil repellency, leveling, and resistance to blocking to a coated substrate comprising adding to a coating base prior to deposition on the substrate a compound of Formula 1

$R_f$-A-OP(O)(O$^-$M$^+$)(OROH)  Formula 1 wherein
- $R_f$ is a $C_2$ to $C_6$ linear or branched perfluoroalkyl optionally interrupted by one, two or three ether oxygen atoms;
- A is $(CH_2CF_2)_m(CH_2)_n$—, $(CH_2)_oSO_2N(CH_3)(CH_2)_p$—, $O(CF_2)_q(CH_2)_r$—, or $OCHFCF_2OE$-;
- m is 0 to 4; n, o, p, and r are each independently 2 to 20; q is 2;
- E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
- M is H or a Group I metal or an ammonium cation $(NH_xR^2_y)^+$ wherein $R^2$ is a $C_1$ to $C_4$ alkyl, x is 0 to 4, y is 0 to 4 and x+y is 4; and
- R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2.

16. The method of claim 14 wherein the coating base is a water dispersed coating, alkyd coating, Type I urethane coating, unsaturated polyester coating, or a floor polish.

17. A method of providing foaming in a medium comprising contacting the medium with a compound of Formula 1

$R_f$-A-OP(O)(O$^-$M$^+$)(OROH)  Formula 1 wherein
- $R_f$ is a $C_2$ to $C_6$ linear or branched perfluoroalkyl optionally interrupted by one, two or three ether oxygen atoms;
- A is $(CH_2CF_2)_m(CH_2)_n$—, $(CH_2)_oSO_2N(CH_3)(CH_2)_p$—, $O(CF_2)_q(CH_2)_r$—, or $OCHFCF_2OE$-;
- m is 0 to 4; n, o, p, and r are each independently 2 to 20; q is 2;
- E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
- M is H or a Group I metal or an ammonium cation $(NH_xR^2_y)^+$ wherein $R^2$ is a $C_1$ to $C_4$ alkyl, x is 0 to 4, y is 0 to 4 and x+y is 4; and
- R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2.

18. The method of claim 17 wherein the medium is an aqueous or brine medium.

19. The method of claim 18 wherein the medium is a cleaning solution or a medium used in stimulation treatment in oil or gas wells or in drilling applications in oil or gas wells.

20. The method of claim 17 wherein the medium is an aggressive medium and the foam disintegrates within 15 minutes.

21. The method of claim 20 wherein the medium is an etching solution or a cleaning solution.

* * * * *